US005804592A

United States Patent [19]
Volicer

[11] Patent Number: 5,804,592
[45] Date of Patent: Sep. 8, 1998

[54] METHOD FOR IMPROVING DISTURBED BEHAVIOR AND ELEVATING MOOD IN HUMANS

[75] Inventor: Ladislav Volicer, Billerica, Mass.

[73] Assignee: Unimed Pharmaceuticals, Inc., Buffalo Grove, Ill.

[21] Appl. No.: 866,511

[22] Filed: May 30, 1997

Related U.S. Application Data

[60] Provisional application No. 60/045,813 May 7, 1997.
[51] Int. Cl.$^6$ ................................................. A61K 31/35
[52] U.S. Cl. .................................... 514/454; 514/221
[58] Field of Search ...................... 514/454, 221

[56] References Cited

U.S. PATENT DOCUMENTS 5,596,106  1/1997  Cullinan et al. ...................... 549/57

OTHER PUBLICATIONS

Cancer Weekly Plus (Abstract) p. 271, 7 Oct. 1996.
Beal et al., Dronabinol as a Treatment for Anorexia Associated with Weight Loss in Patients with Aids, *Journal of Pain and Symptom Management* 10:89–97 (1995).
Katz et al., Studies of Illness in the Aged: The Index of ADL: A standardized Measure of Biological and Psychosocial Function, *JAMA*, 185:914–919 (1963).
Folstein et al., "Mini–Mental State" A Practical Method For Grading The Cognitive State of Patients For The Clinican, *J. Psychiat. Res.*, 12:189–198 (1975).
Ellis et al., Excretion Patterns of Cannabinoid Metabolites After Last Use In A Group Of Chronic Users, *Clin Pharmacol Ther* 38:572–578 (1985).
Volicer et al., Measurement of Severity in Advanced Alzheimer's Disease, *Journal of Gerontology: Medical Sciences* 49:M223–M226 (1994).
Robert Gorter, M.D., Measurement of Anorexia–Cachexia Associated With Cancer and HIV Infection *Oncology* 5:13–17 (1991).
Agurell et al., Pharmacokinetics and Metabolism of $\Delta^1$–Tetrahydrocannabinol and Other Cannabinoids with Emphasis on Man*, *Pharmacological Reviews*, 38:21–43, (1986).
Dackis et al., Persistence of Urinary Marijuana Levels After Supervised Abstinence, *Am J Psychiatry* 139:1196–11989 (1982).
Lawton et al., Observed Affect In Nursing Home Residents With Alzheimer's Disease, *Journal of Gerontology: Psychological Sciences*, 51B:P3–P14 (1996).
McKhann et al., Clinical Diagnosis of Alzheimer's Disease: Report of the NINCDS–ADRADA Work Group* Under The Auspices of Department of Health and Human Services Task Force on Alzheimer's Disease, *Neurology*, 34:939–944 (1984).
Cohen–Mansfield et al., A Description of Agitation in a Nursing Home, *Journal of Gerontology: Medical Sciences*, 44:M77–84 (1989).
Lawton et al., Relationship of Events and Affect in the Daily Life of an Elderly Population, *Psychology and Aging*, 10:469–477 (1995).

*Primary Examiner*—Leonard Schenkman
*Attorney, Agent, or Firm*—Sonnenschein Nath & Rosenthal

[57] ABSTRACT

A method for improving disturbed behavior and negative mood in animals suffering from dementia, particularly humans suffering from Alzheimer's type dementia, by administration of dronabinol.

8 Claims, 2 Drawing Sheets

METHOD FOR IMPROVING DISTURBED BEHAVIOR AND ELEVATING MOOD IN HUMANS

GOVERNMENT SUPPORT

This invention was made with Government support from the Department of Veterans Affairs. The Government may have certain rights in this invention.

RELATED APPLICATIONS

This application claims priority to U.S. provisional patent application, Ser. No. 60/045,813, which was filed on May 7, 1997.

TECHNICAL FIELD OF THE INVENTION

The present invention relates generally to methods for improving disturbed behavior and negative mood in animals, and more specifically to methods for improving disturbed behavior and negative mood in humans suffering from dementia, particularly of the Alzheimer type.

BACKGROUND OF THE INVENTION

Dementia usually denotes a clinical syndrome composed of failing memory and loss of other intellectual functions due to chronic progressive degenerative disease of the brain. Dementia is generally characterized by the gradual loss of intellectual capacities. However, certain behavioral abnormalities and changes in personality are also associated with dementia.

There are several states of dementia of multiple causation and mechanism. Chronic degeneration of neurons is one of many causes.

Most dementing diseases appear during the senium and many others during late adult life. Since the elderly population is increasing both in percentage of population and in absolute numbers in the Western world, the magnitude of medical problems presented is alarming. However, dementias are not a consequence of growing old. They are age-linked diseases.

One of the more common dementias is dementia of the Alzheimer type (DAT). Alzheimer's disease is a degenerative disease which is frequent in occurrence and devastating in nature. Although the disease is extremely uncommon in the young (except for those with Down's syndrome) and rare in those of middle age, it is the most common cause of dementia in the elderly and is associated with distress to the patients and their families and economic loss resulting from costs due to long-term care of patients disabled by the disease. Its prevalence in persons over 80 years of age is believed to be more than twenty percent.

Alzheimer's disease is often associated with a lack of initiative, irritability, loss of interest in things, forgetfulness, change in mood often taking the form of apathy, and excessive lability of mood (i.e., easy fluctuation between laughter and tears on slight provocation).

Dementia of the Alzheimer type also leads to progressive loss of learned behaviors, such as the ability to feed oneself, speech and language disturbances, and lack of coordination of voluntary movement.

A need therefore exists for a method of improving disturbed behavior and elevating mood in patients suffering from dementia.

Dronabinol is a cannabinoid having the chemical designation (6aR-trans)-6a,7,8,10a-tetrahydro-6,6, 9-trimethyl-3-pentyl-6H-dibenzo[b,d]pyran-1-ol and is also referred to as delta-9-tetrahydrocannabinol (delta-9-THC). It is naturally occurring and has been extracted from *Cannabis sativa L.* (marijuana). It can also be chemically synthesized.

Dronabinol is currently marketed in a formulation having the trademark Marinol® for the treatment of anorexia associated with weight loss in patients with AIDS, and for the treatment of nausea and vomiting associated with cancer chemotherapy in patients who have failed to respond adequately to conventional antiemetic treatments. *Physicians'Desk Reference*, 1997.

Studies in AIDS patients have demonstrated an elevated mood or sense of well-being after dronabinol treatment. Gorter, R., *Oncology*, 5 (Supplement): 13–17 (1991); Beal et al., *J. Pain Sympt. Manag.*, 10: 89–97 (1995). However, before the invention herein, dronabinol has not been used or suggested for use in dementia patients, Alzheimer's patients in particular, to improve disturbed behavior or elevate the mood of these patients.

It is, therefore, an object of the present invention to provide a method for improving disturbed behavior and elevating mood in patients suffering from dementia, particularly of the Alzheimer's type.

SUMMARY OF THE INVENTION

In accordance with the present invention, it has now been discovered that certain manifestations associated with dementias may be effectively treated with dronabinol. Specifically, the present invention is directed to a method for improving disturbed behavior in humans suffering from dementia comprising administering an effective amount of dronabinol. The present invention also provides a method for improving negative mood in humans suffering from dementia comprising administering an effective amount of dronabinol.

The methods of the present invention are particularly beneficial when applied to patients suffering from dementia of the Alzheimer's type.

In the methods of the present invention, dronabinol may be administered alone or in combination with a pharmaceutically effective carrier or other pharmaceutically acceptable additives.

Further, the methods of the present invention may be administered in any suitable manner, including orally, buccally, sublingually, subcutaneously, intramuscularly, intravenously, transdermally, and rectally, as well as others.

The quantity of dronabinol administered may vary widely. For example, the amount may be from about 0.01 to 35 mg/kg of body weight administered one to five times per day.

In addition, dronabinol may be administered concurrently or in succession with other medications, i.e. psychoactive medications.

DETAILED DESCRIPTION OF THE INVENTION

Figure 1:
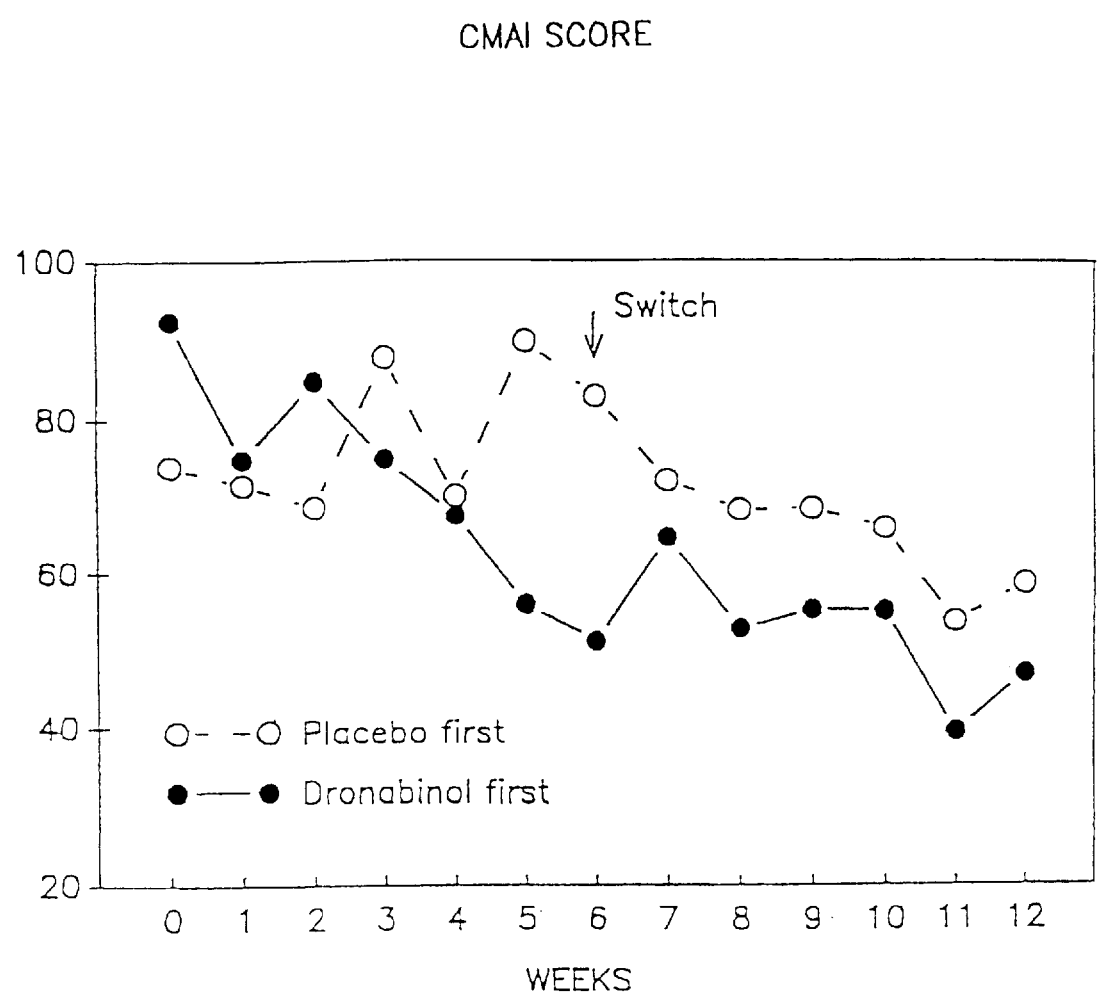
FIG. 1 is a graphical representation identifying changes in the Cohen-Mansfield Agitation Inventory score during the placebo treatment period and the dronabinol treatment period.

In general, the present invention is directed to a method for improving disturbed behavior in humans suffering from dementia by administering an effective amount of dronabinol. The present invention is also directed to a method for elevating negative mood in humans suffering from dementia by administering an effective amount of dronabinol.

The method of the present invention may be used to treat any type of disturbed behavior or negative mood, but most preferably is used to treat disturbed behavior and negative mood associated with dementia in humans. There are a variety of diseases and medical conditions associated with human dementia for which dronabinol may be useful, including Alzheimer's disease, Pick's disease, Huntington's chorea, leukodystrophies, lipid storage diseases such as lipofuscinosis, Creutzfeltd-Jakob disease, multi-infarct dementia, normal pressure hydrocephalus, intracranial masses and posttraumatic dementia. In particular, the method of the present invention improves disturbed behavior and elevates mood in those patients suffering from Alzheimer type dementia.

Although dementias are associated with a multitude of clinical manifestations, in a preferred embodiment of the methods of the present invention, dronabinol may improve any of the numerous disturbed behaviors found in dementia patients, including but not limited to, aimless or wandering pace, inappropriate dress, spitting, cursing or verbal aggression, constant unwarranted request for attention or help, repetitive sentences or questions, hitting, kicking, grabbing onto people, pushing, throwing things, strange noises, screaming, biting, scratching, trying to get to a different place, intentional falling, complaining, negativism, eating/drinking inappropriate substances, hurting themself or others, handling things inappropriately, hiding things, hoarding things, tearing things or destroying property, performing repetitious mannerisms, making verbal sexual advances, general restlessness, and strange movements or making faces.

Further, the method of the present invention may elevate the mood of patients suffering from any of the following moods, including but not limited to, anger, anxiety or fear, and depression or sadness.

Although many types of dementia often strike humans at age 65 and older, the method of the present invention may be applied to any dementia patients regardless of age. Dronabinol may also be administered to a dementia patient regardless of the length of time the patient has been suffering from dementia, be it one day or many years. Further, dronabinol may be administered to a dementia patient for as long as the disturbed behavior improves or the patient's mood is elevated.

Dronabinol is a cannabinoid which has complex effects on the central nervous system (CNS), including central sympathomimetic activity. Cannabinoid receptors have been discovered in neural tissues. It is believed that these receptors may play a role in mediating the effects of dronabinol on the CNS.

Alzheimer's disease and other progressive dementias lead to nerve cell death. This deprives the brain of substances, such as neurotransmitters, which are necessary for normal brain function. These substances stimulate specific receptors and coordinate function of brain cells. Although the endogenous transmitter which stimulates cannabinoid receptors is not known, it is believed that it does exist. Therefore, it is postulated that some symptoms seen in Alzheimer's disease are due to the lack of this endogenous transmitter. Administration of dronabinol may be substituting for the lack of this endogenous transmitter. It is theorized that administration of dronabinol may substitute for the lack of this endogenous transmitter and improve brain function affected by cell loss.

It is further believed that dronabinol may have a prolonged effect on disturbed behavior and mood. For example, it has been reported that tetrahydrocannabinol metabolites are present in the urine as long as 77 days after ingestion of marijuana (Ellis et al., *Clin. Pharmacol. Ther.,* 38: 572–78 (1985)). Dronabinol pharmacokinetics can be described by a four compartment model, with an initial half-life of four hours and a terminal half-life of 25–36 hours. (Agurell et al., *Pharmacol. Rev.,* 38: 21–43 (1986)). However, low levels of dronabinol metabolites have been detected in the urine and feces 2–5 weeks after initiation of a supervised abstinence (Dackis et al., *Am. J. Psychiatry,* 139: 1196–98 (1982)).

Although dronabinol does effect the CNS, it is not believed to increase paranoid reactions and hallucinations, confusion, ataxia, or speech difficulties which would impair cognitive or functional abilities of Alzheimer patients.

In accordance with the methods of the present invention, dronabinol may be administered in the form of a composition, including a pharmaceutical composition, comprising dronabinol. Preferably, the composition additionally comprises a pharmaceutically acceptable carrier.

One skilled in the art will appreciate that suitable methods of administering dronabinol compositions of the present invention to an animal, such as a mammal, are available, and, although more than one route can be used to administer a particular composition, a particular route can provide a more immediate and more effective reaction than another route. Pharmaceutically acceptable carriers are also well-known to those who are skilled in the art. The choice of carrier will be determined, in part, both by the particular composition and by the particular method used to administer the composition. Accordingly, there is a wide variety of suitable formulations of the pharmaceutical compositions of the present invention.

Suitable specific forms of administration include the forms for the oral route, buccal and sublingual forms of administration, subcutaneous, transdermal, intramuscular or intravenous forms of administration and rectal forms of administration, as well as forms for inhalation. For topical application, the compounds according to the invention may be used in creams, ointments or lotions.

The pharmaceutical compositions of the present invention for oral, buccal, nasal, sublingual, subcutaneous, intramuscular, intravenous, topical, transdermal or rectal administration, dronabinol may be administered in sustained or controlled release forms or in dosage unit forms of administration mixed with standard pharmaceutical vehicles to animals or humans. The formulations may conveniently be prepared by any of the methods well known in the art.

Formulations suitable for oral administration can consist of (a) liquid solutions, such as an effective amount of dronabinol dissolved in diluents, such as water, oil, or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Dronabinol, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers such as acetate and phosphate, toxicity adjusting agents, such as sodium chloride, pH adjusting agents, such as hydrochloric and phosphoric acid, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

In a preferred embodiment, dronabinol is administered as an oral capsule composition containing 2.5 mg, 5 mg or 10 mg dronabinol, sesame oil, gelatin, glycerin, methylparaben, propylparaben, and titanium dioxide.

The dose administered to an animal, particularly a human, in the context of the present invention should be sufficient to effect a therapeutic response over a reasonable time frame. The dose will be determined by the strength of the particular compositions employed and the condition of the person, as well as the body weight of the person to be treated. The size of the dose also will be determined by the existence, nature, and extent of any adverse side-effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of dronabinol in pharmaceutical compositions for oral administration is 0.05 to 15% (by weight). A preferred concentration is from 0.02 to 5%. A more preferred concentration is from 0.1 to 4%. More preferably, 0.03 to 0.06 mg/kg body weight per day is administered orally, and most preferably, a 2.5 mg oral dosage form is administered two times per day. The most preferred dosage for extracorporeal administration is in the range from about 0.1 mg/kg to 5 mg/kg of body weight per day. For the rectal, topical (including buccal and sublingual) or transdermal route of administration, the preferred dosage thereof (estimated as the base) is in the range 0.05 mg/kg to 20 mg/kg of body weight per day. Although dronabinol may be administered as needed, preferably, dronabinol is administered one to five times per day.

Dronabinol may be administered concurrently with other necessary medications. For example, one or more psychoactive medications may be administered before, concurrently and after treatment with dronabinol. Examples of such psychoactive medications include, but are not limited to, antidepressants, neuroleptics, and benzodiazepines. Specific neuroleptic medications include, but are not limited to, perphenazine, thiothixene, haloperidol, and thioridazine. Specific benzodiazepines include, but are not limited to, lorazepam and alprazolam. Specific antidepressants include, but are not limited to, sertraline, trazodone and desipramine.

Although the preferred embodiment of the present invention is the treatment of dementia, particularly of the Alzheimer type, in humans, the methods of the present invention may be used to treat disturbed behavior and elevate mood in animals of any kind. Examples of suitable animals, include but are not limited to dogs, pigs, sheep, horses, cows, and cats.

All publications cited to or referenced herein are incorporated by reference in their entirety.

The present invention will be further illustrated by the following example. This example serves to illustrate further the present invention and is not intended to limit the scope of the invention.

EXAMPLE

Each patient in the this example was diagnosed with "probable" DAT by a neurologist according to DSM III-R and NINCDS-ARDDA criteria. These generally accepted criteria include deficits in two or more areas of cognition, progressive worsening of memory and other cognitive functions, no disturbances of consciousness, and absence of systemic disorders or other brain disease that in and of themselves could account for the progressive deficits in memory and cognition. (McKhann et al., *Neurology*, 34: 939–944 (1984). Each patient received physical examination and laboratory examination including complete blood count with differential, liver function tests, thyroid function tests including TSH, iron binding capacity, BUN, creatinine, and electrolytes.

The severity of dementia in each patient was measured by the Mini-mental Status Examination (MMSE). MMSE is generally known in the art and is generally described in Folstein et al., *J. Psychiatr. Res.*, 12: 189–198 (1975), Katz Activity of Daily Living scale (Katz ADL) (Katz et al., *JAMA*, 185: 914–19 (1963), and Bedford Alzheimer Nursing Scale-Severity (BANS-S) (Volicer et al., *J. Gerontol.*, 49: M223–26 (1994). This data is reported in Table 1.

TABLE 1

| Characteristic | Mean ± S.D.* | Range |
| --- | --- | --- |
| Age (years) | 72.7 ± 4.9 | 65–82 |
| Gender | 11 males, 1 female | |
| Duration of DAT (years) | 7.0 ± 4.1 | 2–16 |
| Duration of long-term care before beginning of the study (months) | 17.4 ± 21.9 | 2.6–81.0 |
| Mini-mental Status Examination score (11) | 4.0 ± 7.4 | 0–20 |
| Katz Activity of Daily Living Score (12) | 5.7 ± 0.6 | 4–6 |
| Bedford Alzheimer Nursing Scale-Severity score (13) | 17.5 ± 3.0 | 13–22 |

*S.D. refers to standard deviation.

The patients included in the analysis were all 65 years old or older and all but one were males. Duration of DAT varied from 2 to 16 years and most patients had been in institutional long-term care for many months before the onset of the study. Most also suffered from severe dementia; the MMSE score was 0 in 8 subjects. Patients also were severely impaired in activities of daily living; 9 were dependent in all 6 activities. BANS-S score, which detects progression of the disease even in the severe stage indicated moderate to severe impairment.

Eleven of the patients were on a psychoactive medication before the beginning of dronabinol study and were maintained on the same medication during the study period. Four patients were receiving regular doses of neuroleptics (perphenazine, thiothixene, haloperidol or thioridazine), 4 patients were receiving regular doses of benzodiazepienes (3 lorazepam and one alprazolam), and 8 patients were receiving regular doses of antidepressants. The antidepressants included sertraline (8 patients), trazodone (4 patients) and desipramine (1 patient). Three patients were on both sertraline and trazodone, and one patient was switched from trazodone to doxepin. Antidepressant treatment was initiated at least 4 weeks before the start of the study and the mean duration of antidepressant treatment before study initiation was 7 months. Eleven patients had orders for psychoactive medications as needed (PRN). These included lorazepam in 4 patients and alprazolam, trazodone, doxepin, haloperidol, perphenazine and thioridazine in one patient each. The patients received these medications very rarely, on the average 9.7 doses/6 weeks during the placebo administration and 7.2 doses/6 weeks during dronabinol treatment.

A double blind placebo-controlled crossover design was used with each period of study lasting six weeks. Dronabinol or placebo was administered on a fixed dose schedule, 2.5 mg capsule or identically looking placebo capsule every morning and noon. Subjects were randomly assigned to placebo first or dronabinol first groups. Possible side effects were determined every week by asking the primary caregivers if the patient experienced any of a list of possible symptoms. A list of these symptoms observed in twelve patients over seventy weeks is identified in Table 2 below.

TABLE 2

| SYMPTON | DRONABINOL | | | | PLACEBO | | | |
|---|---|---|---|---|---|---|---|---|
| | Patients | | Weeks | | Patients | | Weeks | |
| | n* | % | n | % | n | % | n | % |
| Anxiety/nervousness | 11 | 92 | 37 | 53 | 12 | 100 | 43 | 61 |
| Emotional lability | 11 | 92 | 32 | 46 | 10 | 83 | 36 | 51 |
| Tiredness | 9 | 75 | 25 | 36 | 5 | 42 | 15 | 21 |
| Somnolence | 8 | 67 | 29 | 41 | 4 | 33 | 12 | 17 |
| Euphoria | 7 | 58 | 31 | 44 | 5 | 42 | 16 | 23 |
| Paranoid reaction | 4 | 33 | 16 | 23 | 5 | 42 | 18 | 26 |
| Hallucination | 4 | 33 | 11 | 16 | 5 | 42 | 16 | 23 |
| Depression | 2 | 16 | 4 | 6 | 2 | 16 | 4 | 6 |
| Ataxia | 2 | 16 | 6 | 8 | 2 | 16 | 3 | 4 |
| Muscle pain | 2 | 16 | 7 | 10 | 1 | 8 | 3 | 4 |
| Diarrhea | 2 | 16 | 3 | 4 | | | | |
| Flushing | 1 | 8 | 2 | 3 | 2 | 16 | 2 | 3 |
| Increased confusion | 1 | 8 | 2 | 3 | 2 | 16 | 2 | 3 |
| Sweating | 1 | 8 | 2 | 3 | 1 | 8 | 1 | 1 |
| Increased speech difficulty | | | | | 1 | 8 | 1 | 1 |
| Headache | 1 | 8 | 1 | 1 | | | | |
| Nightmares | | | | | 1 | 8 | 1 | 1 |

*n refers to the number of patients experiencing the listed effect and % identifies the percentage of total patients experiencing the effect.

In addition to the listed effects, one incidence of seizure in a dronabinol treated patient was observed.

Baseline measurements were taken the week prior to randomization and treatment initiation. Behavior measures were obtained weekly for the 12 week duration of the trial. Repeated measures on these variables were therefore available for six weeks on dronabinol and six weeks on placebo for each subject.

The extent of disturbed behavior exhibited by each patient was determined each week by interview with primary caregivers who were familiar with the patients' behavior and with rating scales. The disturbed behavior was measured by the Cohen-Mansfield Agitation Inventory (CMAI)(Cohen-Mansfield et al., J. Gerontol. Med. Sci., 44: M77–84 (1989)) which is a widely used instrument with good psychometric properties. Twenty nine items of this inventory are rated by frequency (from 1=never to 7=constantly or almost constantly) and by disruptiveness (from 1=not at all to 5=extremely). For each observation period, the total score was calculated by multiplying the frequency and disruptiveness of individual items and adding the products. The CMAI items observed are identified in Table 3 below.

TABLE 3

CMAI BEHAVIOR ITEMS OBSERVED

Pace, aimless wandering
Inappropriate dress, disrobing
Spitting (include at meals)
Cursing or verbal aggression
Constant unwarranted request for attention or help
Repetitive sentences or questions
Hitting (including self)
Kicking
Grabbing onto people
Throwing things
Strange noises (weird laughter or crying)
Screaming
Biting
Scratching
Trying to get to a different place (e.g. out of the ward)
Intentional falling
Complaining
Negativism
Eating/drinking inappropriate substances
Hurt self or other (hot water, etc.)
Handling things inappropriately
Hiding things
Hoarding things
Tearing things or destroying property
Performing repetitious mannerisms
Making verbal sexual advances
General restlessness
Strange movements, make faces Patients' affect was measured using Lawton Observed Affect Scale - Past (Lawton et al., J. Gerontol. [B], 51B: P3–14 (1996)). This scale consists of six items, three measuring positive affect (pleasure, interest and contentment) and three measuring negative affect (anger, anxiety/fear and depression/sadness) on a 5 point scale (from 1=never to 5=more than 3 time a day). The negative and positive affect scores were calculated by adding scores of the appropriate items.

Statistical analysis was performed using Statistix 4.1 (Analytic Software). Repeated measures ANOVA for the 12 weeks of the study was done to test for effects of order, time and treatment on-study variables.

FIG. 1 is a graphical representation showing the CMAI score during the placebo and dronabinol phases of the study. Disturbed behavior decreased during dronabinol treatment (F(order×treatment)=2.78, df=1,143, p=0.12) and this decrease in disturbed behavior persisted during the placebo period following treatment with dronabinol. When the CMAI scores were expressed as percentage of the baseline, there was a significant order ×time interaction (F=2.35 (order×time,), df=5,143, p=0.05).

Figure 2:
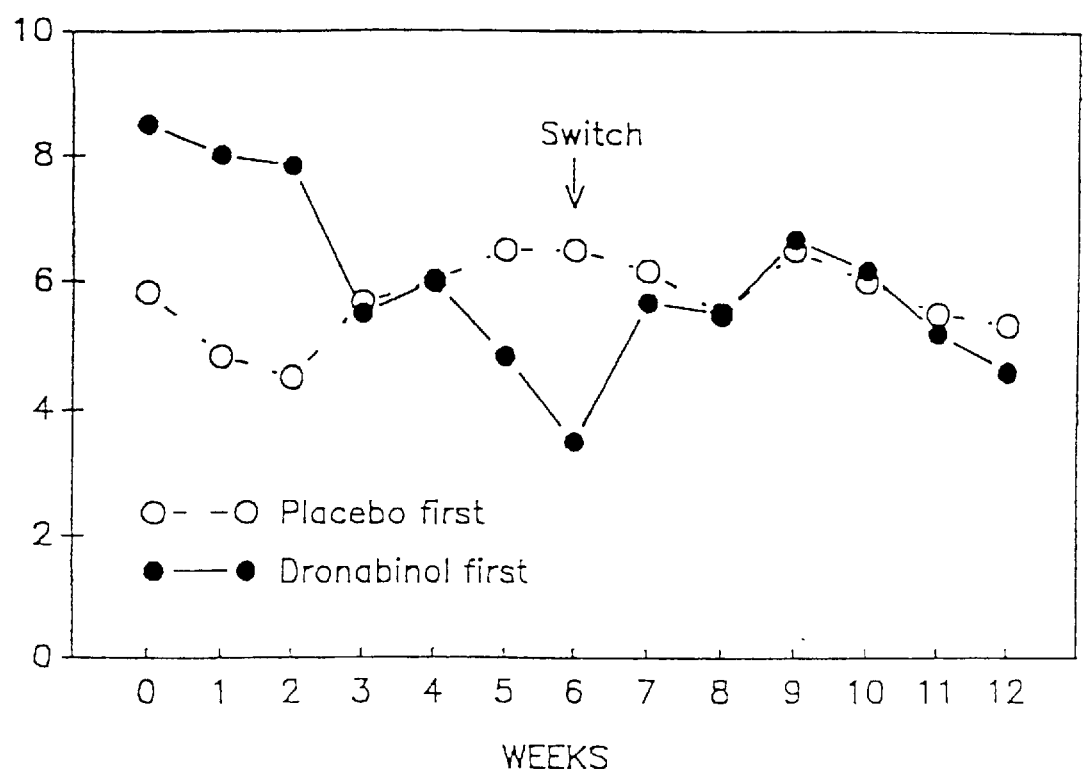
FIG. 2 is a graphical representation identifying changes in the Negative Affect score during the placebo treatment period and the dronabinol treatment period.

FIG. 2 is a graphical representation of the changes in the negative affect score during the placebo and dronabinol phases. Negative affect decreased during the 12 weeks study period (F(time)=2.46, df=5,143, p=0.045) and it decreased more while patients were on dronabinol then during the placebo periods (F(time×treatment)=3.98, df=5,143, p=0.004). Further, the decrease was greater for those who received dronabinol first, compared to those who received placebo first (F(order×time)=5.45, df=5,143, p<0.0005). In contrast, positive affect remained similar during both treatments (dronabinol and placebo) and treatment periods (the six week dronabinol phase and the six week placebo phase).

Decreased agitation was observed using two scales: CMAI and Observed Affect Scale. The negative part of the Observed Affect Scale includes two items (anger and anxiety/fear) which are commonly present in patients during agitated behaviors. The third item, depression/sadness was rarely observed as can be seen from Table 2. Thus both scales measured similar disruptive behaviors. It is possible that this effect was partly due to somnolence, which was twice as common in patients treated with dronabinol than in patients on placebo.

The effect of dronabinol on disturbed behavior carried over to the following placebo period. There was no difference in the disturbed behavior in the second treatment period. This prolonged change in disturbed behavior could be due to a long-term effect of dronabinol.

Dronabinol treatment did not change the Positive Affect, although euphoria as an adverse reaction was reported more frequently and in more patients during the dronabinol treatment than during placebo periods. It is possible that the Positive Affect items represent more a degree of patient's engagement than patient's mood (Lawton et al., *Psychol. Aging*, 3: 469–477 (1995)).

While this invention has been described with an emphasis upon preferred embodiments, it will be obvious to those of ordinary skill in the art that variations in the preferred methods of the present invention may be used and that it is intended that the invention may be practiced otherwise than as specifically described herein, Accordingly, this invention includes all modifications encompassed within the spirit and scope of the invention as defined by the following claims.

What is claimed:

1. A method of treating humans suffering from dementia comprising administering a therapeutically effective amount of dronabinol to said humans.

2. The method of claim 1, wherein said dementia comprises the Alzheimer's type.

3. The method of claim 1, wherein said dronabinol is administered in combination with a pharmaceutically effective carrier.

4. The method of claim 1, further comprising administration of a psychoactive medication.

5. The method of claim 4, wherein said psychoactive medication is selected from the group consisting of antidepressants, neuroleptics, and benzodiazepines.

6. The method of claim 1, wherein dronabinol is administered to said humans orally.

7. The method of claim 6, wherein dronabinol is administered in an amount from about 0.03 to about 0.06 mg/kg body weight per day.

8. The method of claim 6, wherein 2.5 mg of dronabinol is administered two times per day.

* * * * *